US008034816B2

(12) United States Patent
Linz et al.

(10) Patent No.: US 8,034,816 B2
(45) Date of Patent: Oct. 11, 2011

(54) HYDRATES AND POLYMORPHS OF 4-[[(7R)-8-CYCLOPENTYL-7-ETHYL-5,6,7,8-TETRAHYDRO-5-METHYL-6-OXO-2-PTERIDINYL]AMINO]-3-METHOXY-N-(1-METHYL-4-PIPERIDINYL)-BENZAMIDE, PROCESS FOR THEIR MANUFACTURE AND THEIR USE AS MEDICAMENT

(75) Inventors: Guenter Linz, Mittelbiberach (DE); Peter Sieger, Mittlebiberach (DE); Gerd F. Kraemer, Eberhardzell (DE); Rolf Herter, Biberach (DE); Matthias Hoffmann, Mittlebiberach (DE); Werner Rall, Mittelbiberach (DE); Rolf Schmid, Baltrigen (DE)

(73) Assignee: Boehringer Ingelheim International GmbH (DE)

( * ) Notice: Subject to any disclaimer, the term of this patent is extended or adjusted under 35 U.S.C. 154(b) by 154 days.

(21) Appl. No.: 12/478,183

(22) Filed: Jun. 4, 2009

(65) Prior Publication Data

US 2009/0298840 A1 Dec. 3, 2009

Related U.S. Application Data

(63) Continuation of application No. 11/197,634, filed on Aug. 4, 2005, now Pat. No. 7,728,134.

(30) Foreign Application Priority Data

Aug. 14, 2004 (DE) ................................ EP04019366

(51) Int. Cl.
*C07D 475/00* (2006.01)
*A61K 31/497* (2006.01)
*A61P 35/00* (2006.01)

(52) U.S. Cl. .................... 514/253.01; 544/258
(58) Field of Classification Search .................. 544/258; 514/253.01
See application file for complete search history.

(56) References Cited

U.S. PATENT DOCUMENTS

| | | | |
|---|---|---|---|
| 4,957,922 A | 9/1990 | Lammens et al. |
| 5,167,949 A | 12/1992 | Ferrand et al. |
| 5,198,547 A | 3/1993 | Bailey et al. |
| 5,424,311 A | 6/1995 | Billhardt-Troughton et al. |
| 5,698,556 A | 12/1997 | Chan |
| 6,096,924 A | 8/2000 | Studer et al. |
| 6,156,766 A | 12/2000 | Arita et al. |
| 6,174,895 B1 | 1/2001 | Kleinman |
| 6,605,255 B2 | 8/2003 | Kroll et al. |
| 6,806,272 B2 | 10/2004 | Bauer et al. |
| 6,861,422 B2 | 3/2005 | Hoffmann et al. |
| 6,875,868 B2 | 4/2005 | Bonnert et al. |
| 7,238,807 B2 | 7/2007 | Duran et al. |
| 7,241,889 B2 | 7/2007 | Hoffmann et al. |
| 7,332,491 B2 | 2/2008 | Grauert et al. |
| 7,371,753 B2 | 5/2008 | Stadtmueller et al. |
| 7,414,053 B2 | 8/2008 | Grauert et al. |
| 7,439,358 B2 | 10/2008 | Linz et al. |
| 7,547,780 B2 | 6/2009 | Grauert et al. |
| 7,625,899 B2 | 12/2009 | Hoffmann et al. |
| 7,626,019 B2 | 12/2009 | Duran et al. |
| 7,629,460 B2 | 12/2009 | Grauert et al. |
| 7,700,769 B2 | 4/2010 | Grauert et al. |
| 7,723,517 B2 | 5/2010 | Grauert et al. |
| 7,728,134 B2 | 6/2010 | Linz et al. |
| 7,750,152 B2 | 7/2010 | Hoffman et al. |
| 7,759,347 B2 | 7/2010 | Hoffmann |
| 7,759,485 B2 | 7/2010 | Linz et al. |
| 7,807,831 B2 | 10/2010 | Grauert et al. |
| 7,816,530 B2 | 10/2010 | Grauert |
| 2002/0183292 A1 | 12/2002 | Pairet et al. |
| 2002/0183293 A1 | 12/2002 | Banerjee et al. |
| 2003/0130286 A1 | 7/2003 | Denny et al. |
| 2004/0029885 A1 | 2/2004 | Bauer et al. |
| 2004/0147524 A1 | 7/2004 | Bauer et al. |
| 2004/0176380 A1 | 9/2004 | Hoffmann et al. |
| 2005/0014760 A1 | 1/2005 | Hoffmann et al. |
| 2005/0014761 A1 | 1/2005 | Hoffmann et al. |
| 2005/0148501 A1 | 7/2005 | Palmer et al. |
| 2005/0159414 A1 | 7/2005 | Nickolaus et al. |
| 2005/0165010 A1 | 7/2005 | Nickolaus et al. |
| 2006/0004014 A1 | 1/2006 | Hoffmann et al. |
| 2006/0009457 A1 | 1/2006 | Hoffmann et al. |
| 2006/0025411 A1 | 2/2006 | Hoffmann et al. |
| 2006/0035902 A1 | 2/2006 | Linz et al. |
| 2006/0035903 A1 | 2/2006 | Mohr et al. |
| 2006/0046989 A1 | 3/2006 | Grauert et al. |
| 2006/0047118 A1 | 3/2006 | Stadtmueller et al. |

(Continued)

FOREIGN PATENT DOCUMENTS

| | | |
|---|---|---|
| CA | 2458699 | 3/2003 |
| CA | 2517020 | 9/2004 |
| CA | 2517010 | 11/2004 |
| CA | 2576290 | 2/2006 |
| EP | 143478 | 6/1985 |
| EP | 347146 | 12/1989 |
| EP | 399856 | 11/1990 |

(Continued)

OTHER PUBLICATIONS

ACPS Meeting, Background Information. "Scientific considerations of plymorphism in pharmaceutical solids: abbreviated new drug applications". Oct. 2002.

Ahlenius, T. List of cardiovascular disorder/diseases. Ahlenius, Karolinska Institutet. Stockholm, Sweden. Cardiovascular Diseases, p. 1-34, Apr. 2007.

(Continued)

*Primary Examiner* — James O Wilson
*Assistant Examiner* — Cecilia M Jaisle
(74) *Attorney, Agent, or Firm* — Michael P. Morris; Julie A. Scott

(57) ABSTRACT

Disclosed are hydrates and polymorphs of 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide, processes for preparing them and their use as pharmaceutical compositions.

14 Claims, 9 Drawing Sheets

U.S. PATENT DOCUMENTS

| | | | |
|---|---|---|---|
| 2006/0052383 | A1 | 3/2006 | Grauert et al. |
| 2006/0058311 | A1 | 3/2006 | Munzert et al. |
| 2006/0074088 | A1 | 4/2006 | Munzert et al. |
| 2006/0079503 | A1 | 4/2006 | Schwede et al. |
| 2007/0208027 | A1 | 9/2007 | Duran et al. |
| 2007/0213528 | A1 | 9/2007 | Duran et al. |
| 2007/0213529 | A1 | 9/2007 | Duran et al. |
| 2007/0213530 | A1 | 9/2007 | Duran et al. |
| 2007/0213531 | A1 | 9/2007 | Duran et al. |
| 2007/0213534 | A1 | 9/2007 | Duran et al. |
| 2007/0219369 | A1 | 9/2007 | Duran et al. |
| 2008/0108812 | A1 | 5/2008 | Grauert et al. |
| 2008/0113992 | A1 | 5/2008 | Grauert et al. |
| 2008/0171747 | A1 | 7/2008 | Hoffman et al. |
| 2008/0177066 | A1 | 7/2008 | Linz et al. |
| 2008/0194818 | A1 | 8/2008 | Grauert et al. |
| 2008/0221099 | A1 | 9/2008 | Munzert et al. |
| 2008/0293944 | A1 | 11/2008 | Hoffmann et al. |
| 2008/0319190 | A1 | 12/2008 | Grauert et al. |
| 2008/0319192 | A1 | 12/2008 | Grauert et al. |
| 2008/0319193 | A1 | 12/2008 | Grauert et al. |
| 2009/0018333 | A1 | 1/2009 | Grauert et al. |
| 2009/0023733 | A1* | 1/2009 | Cage et al. ............... 514/235.5 |
| 2009/0030004 | A1 | 1/2009 | Linz et al. |
| 2009/0124628 | A1* | 5/2009 | Hoffmann et al. ............ 514/249 |
| 2009/0143379 | A1 | 6/2009 | Mohr et al. |
| 2009/0238828 | A1 | 9/2009 | Munzert et al. |
| 2009/0280115 | A1 | 11/2009 | Maier et al. |
| 2009/0298840 | A1 | 12/2009 | Linz et al. |
| 2010/0029642 | A1 | 2/2010 | Hoffmann et al. |
| 2010/0249412 | A1 | 9/2010 | Linz et al. |
| 2010/0249458 | A1 | 9/2010 | Linz et al. |
| 2010/0280037 | A1 | 11/2010 | Linz et al. |
| 2010/0324288 | A1 | 12/2010 | Hoffmann et al. |

FOREIGN PATENT DOCUMENTS

| | | |
|---|---|---|
| EP | 429149 | 5/1991 |
| ES | 2287583 | 12/2007 |
| RU | 2002125451 A | 1/2004 |
| WO | 9609045 | 3/1996 |
| WO | 9634867 | 11/1996 |
| WO | 9636597 | 11/1996 |
| WO | 9811893 | 3/1998 |
| WO | 0119825 | 3/2001 |
| WO | 0170741 | 9/2001 |
| WO | 0178732 | 10/2001 |
| WO | 02057261 | 7/2002 |
| WO | 02076954 | 10/2002 |
| WO | 02076985 | 10/2002 |
| WO | 03020722 | 3/2003 |
| WO | 03093249 | 11/2003 |
| WO | 2004014899 | 2/2004 |
| WO | 2004076454 | 9/2004 |
| WO | 2004093848 | 11/2004 |
| WO | 2005067935 | 7/2005 |
| WO | 2006/018182 | 2/2006 |
| WO | 2006/018221 | 2/2006 |
| WO | 2006018185 | 2/2006 |
| WO | 2006018220 | 2/2006 |
| WO | 2006018221 | 2/2006 |
| WO | 2006021378 | 3/2006 |
| WO | 2007090844 | 8/2007 |
| WO | 2009019205 | 2/2009 |

OTHER PUBLICATIONS

Ahmad, N. "Polo-like kinase (Plk) 1: a novel target for the treatment of prostate cancer". Dept of Dermatology, Univ. Wisconsin, pp. 3-5, 2003.

Arnold, K. "Collaboration to play key role in NCI's future, director says". Journal of the National Cancer Institute, Jun. 5, 2002, pp. 790-792, vol. 94, No. 11.

BBC News/Health, Killer Breast Cancern Therapy Hope, www.newsvote.bbc/co./uk, downloaded Mar. 26, 2009.

Bennett, J.C., et al., "Textbook of Medicine", Part XIV, Oncology, 1997.

Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.

Dipolar aprotic solvent. Exhibit A, IUPAC Compendium of Chemical Terminology, 2nd Edition, 1997.

Doerwald, F.Z. "Side reactions in organice synthesis". 2005.

Eurasian Opinion, Appln No. 2007/00389/28, Maly Slatoustinsky per., d.10, kv.15, 101000 Moscow, Russia, "EVROMARKPAT", 2007.

Ferrand, G., et al., "Synthesis and potential antiallergic activity of new pteridinones and related compounds". Eur. J. Med. Chem, 31, 1996, pp. 273-280. XP—2246920.

Giron, G. "Thernal analysis and calorimetric methods in the characterization of plymorphs and solvates". Thermochimica Acta 248, 1995, pp. 1-59.

Goodman-Gilman's "The Pharmacological Basis of Therapeutics". Ninth edition, 1996, pp. 1225-1271.

Ito, Y., et al., "Polo-like kinase 1 (PLK) expression is associated with cell proliferative activity and cdc2 expression in malignant-lymphoma of the thyroid". Anticancer Research, 2004, vol. 24, No. 1, pp. 259-263.

Jaworska, J., et al., "Review of methods for assessing the applicability domains of SARS and QSARS". Sponsor: The European Commission—Joint Research Ctr., Institute for Health and Consumer Protection—ECVAM, Italy, 2004.

Kashima, M. K. et al., "Expression of polo-like kinase (PLK1) in non-Hodgkin's lymphomas". NCBI, PubMed, 2005.

Kimball, S. D. et al., "Cell cycle kinases and checkpoint regulation in cancer". Annual Reports in Medicinal Chemistry, 36, Chapter 14, pp. 139-148, 2001.

Leukemia & Lymphoma Society—Disease Information-Lymphoma. www.leukemia-lymphoma.org/all_page?item_id-7030, downloaded Mar. 26, 2009.

Leukemia & Lymphoma Society—Disease Information. www.leukemia-lymphoma.org/all_page?item_id-7026, downloaded Mar. 26, 2009.

Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.

Masuda, Y. et al., "B-Hydroxyisovalerylshikonin induces apoptosis in human leukemia cells by inhibiting the activity of a polo-like kinase 1 (PLK)". 2003, Oncogene, 22, pp. 1012-1023.

MedlinePlus: Bacterial Infections. www.nim.nih.gov/medlineplus/print/bacterialinfections.htm, downloaded Mar. 26, 2009.

MedlinePlus: Viral Infections. www.nim.nih.gov/medlineplus/print/viralinfections.htm, downloaded Mar. 26, 2009.

Merck Manual of Medical Information—Home Edition, Section 17. "Parasitic Infections". Chapter 184, 2003.

Mito, K., et al., "Expression of polo-like kinase (PLK1) in non-Hodgkin's lymphomas". NCBI, PubMed, 2005, Leuk. Lymphoma, 46(2), pp. 251-231.

Nagao, K. et al., "Effect of MX-68 on airway inflammation and hyperresponsiveness in mice and guinea-pigs". Journal of Pharmacy and Pharmacology, JPP 2004, 56, pp. 187-196.

National Institute of Neurological Disorders, Index Stroke, 2006.

National Kidney Foundation: Chronic Kidney Disease (CKD). www.kidney.org/kidneydisease/ckd/index.cfm, downloaded Mar. 26, 2009.

Norman, P. "PDE4 inhibitors". 1999, Ashley Publications Ltd., pp. 1101-1118.

Office Action mailed Dec. 10, 2003 for U.S. Appl. No. 10/226,710, filed Aug. 23, 2002.

Office Action mailed Apr. 28, 2004 for U.S. Appl. No. 10/374,876, filed Feb. 26, 2003.

Ohio Dept of Health, "Brain and Other Central Nervous System Cancer in Ohio, 1997-2001". Sep. 2004, pp. 1-4.

Organic Chemistry, Grupo Editorial Iberoamerica, Section 13, 3, pp. 301-302, 1983.

Rylander, P.N. "Hydrgenation Methods". 1985, Chapter 13.

Rylander, P.N. "Hydrgenation Methods". 1985, Chapters 3, 4.

Rylander, P.N. "Hydrgenation Methods". 1985, Chapters 8, 9, 10, 11.

Rylander, P.N. "Hydrgenation Methods". 1985, Chapter 5, 6, 7.

Rylander, P.N., "Hydrogenation Methods". 1985, Chapters 1, 2.

Santing, R. E. et al., "Brochodilatory and anti-inflammatory properties of inhaled selective phosphodiesterase inhibitors in a guinea pig model of allergic asthma". European Journal of Pharmacology, 429, 2001, pp. 335-344.

Savelli, F. et al., "Heterotricyclic system Part II—synthesis of new pyrido[1'2':4,5]pyrazino[3,2-d] pyrimidines". Bollettino Chimico Farmaceutico, 131(8), Sep. 1992, pp. 309-312.

Snyder, J. S. et al., "Common bacteria whose susceptibility to antimicrobials is no longer predictable". NCBI, PubMed, 2000, J. Med. Liban, 48, pp. 208-214.

Souillac, P. et al., "Characterization of delivery systems, differential scanning calorimetry". pp. 212-227, 2007.

Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21-pp. 129-133.

Takai, N. et al., "Polo-like kinases (PLKs) and cancer". Oncogene, 2005, 24, pp. 287-291.

Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.

Turner, W.W.et al., "Recent advances in the medicinal chemistry of antifungal agents". Current Pharmacutical Design, 1996, 2, pp. 209-224.

Verschuren, E.W. et al., "The cell cycle and how it is steered by Kaposi's sarcoma-associated herpesvirus cyclin". Journal of General Virology, 2004, 85, pp. 1347-1361.

Vippagunta, S. R. et al., "Crystalline solids". Advanced Drug Delivery Reviews, 48, 2001, pp. 3-26.

Viral Defense Foundation. www.viraldefense.org/mission.htm, downloaded Mar. 26, 2009.

Visiting Nurse Association of America. www.vnaa.org/gen/Germ_Protection_Center_Cold_and_Flu_Resources,html, downloaded Mar. 26, 2009.

Voskoglou-Nomikos, T. et al., "Clinical predictive value of the in vitro cell line, human xenograft, and mouse allograft preclinical cancer models". Clinical Cancer Research vol. 9, 2003, pp. 4227-4239.

Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, pp. 659-668, 2002.

Wagner, G. et al., "Synthesis of new phrido[3',2':4,5] thieno '3,2-d] 1,2,3-triazine derivatives as antianaphylactics". Biosciences Dept of the University of Leipzig, Pharmazie (Pharmacy), 48, 19923, vol. 7, pp. 514-518, 2002.

Webster's Comprehensive Dictionary, 1996, pp. 1013-1014.

Wikipedia. "Melting Point", 2009.

Wolf, D. E.et al., "The structure of rhizopterin". Contribution from the Research Labs of Merck and Co. Inc. Nov. 1947, Journal of American Chem. Soc., vol. 69, pp. 2753-2759. XP002352205.

Ghandi, L, et al., "An Open-Label Phase II Trial of the PLK Inhibitor BI 2536 in Patients with Sensitive Relapse Small Cell Lung Cancer". ASCO Meeting 2009.

Chen, J.X. et al., "Parallel differentiated recognition of ketones and acetals". Angewandte Chemie Int. Ed, vol. 37, Issue 1/2, p. 91-93, 1998.

Dyson, G, et al. "The Chemistry of Synthetic Drugs". 1964, p. 12-19.

International Search Report for PCT/EP2005/008736 mailed Nov. 30, 2005.

Jamieson, C. et al., "Application of ReactArray Robotics and Design of Experiments Techniques in Optimisation of Supported Reagent Chemistry". Org. Proc. Res. & Dev., 2002, 6, p. 823-825.

Mashkovkii, M.D., "Medicaments". Moscow, Novaja Volna, 2001, vol. 1, p. 11.

Mashkovskii, M.D. "Drugs", Handbook for Doctors, 1993, Part I, Ch.1, p. 8.

Mayer, SF, et al., "Enzyme-initiated domino (cascase) reactions". Chem. Soc. Rev, 2001, p. 332-339.

McInnes, C. "Inhibitors of polo-like kinase reveal roles in spindle-pole maintenance". Nature Chemical Biology, vol. 2, No. 11, Nov. 2006, p. 608.

Mikhailov, I.B., Principles of Rational Pharmacotherapy. Handbook for clinical pharmacology for students of pediatric and medical faculties of medical high schools, St. Petersburg, Russia, "Foliant", 1999, p. 25.

Neidle, S. ed., "Cancer Drug Design and Discovery", Elsevier/Academic Press, 2008, p. 427-431.

Rocha Lima, C.M. et al. "Randomized phase II trial of gemcitabine plus irinotecan or docetaxel uin stage IIIB or stage IV NSCLC" Annals of Oncology, 15(3), p. 410-418, 2004.

Science, vol. 310, Oct. 21, 2005, p. 409, Chemistry: One After Another.

Steegmaier, M. et al. "BI 2536, a potent and selective inhibitor of polo-like kinase 1, inhibits tumor growth in vivo". Current Biology, 2007, 17(4), p. 316-322.

Stephenson, D.T. et al. "The effects of a selective dopamine D2 receptor agonist on behavioral and pathological outcome in 1-methl-4-phenyl-1,2,3,6-tetrahydropyridine-treated squirrel monkeys". J. Pharmacology and Experimental Therapeutics, vol. 303, No. 2, 2002, p. 1257.

Turner, S., "The Design of Organic Syntheses". Elsevier, 1976, pp. 10 and 149.

Walsh, F. "No "Magic Bullet" Cure for Cancer". BBC News Feb. 1, 2007, http://news.bbc,co.uk/2/health/6310697.stm, downloaded Jul. 6, 2010.

* cited by examiner

HYDRATES AND POLYMORPHS OF 4-[[(7R)-8-CYCLOPENTYL-7-ETHYL-5,6,7,8-TETRAHYDRO-5-METHYL-6-OXO-2-PTERIDINYL]AMINO]-3-METHOXY-N-(1-METHYL-4-PIPERIDINYL)-BENZAMIDE, PROCESS FOR THEIR MANUFACTURE AND THEIR USE AS MEDICAMENT

APPLICATION DATA

This application is a continuation application of U.S. Ser. No. 11/197,634 filed on Aug. 4, 2005 now U.S. Pat. No. 7,728,134 which claims benefit to European Patent Application EP 04 019 366.6 Aug. 14, 2004.

FIELD OF INVENTION

The present invention relates to new hydrates and new polymorphs of the 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide, processes for preparing them and their use as pharmaceutical compositions.

BACKGROUND TO THE INVENTION

The compound 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide as a polo-like kinase (PLK) plays an important part in the regulation of the eukaryotic cell cycle.

The compound 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide has the structure of the following formula (I).

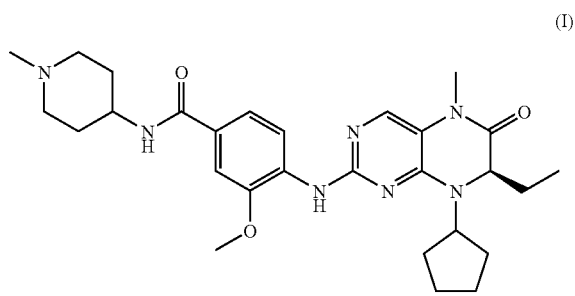

(I)

Similar dihydropteridinones are described in WO 03/020722.

DETAILED DESCRIPTION OF THE INVENTION

Figure 1A:
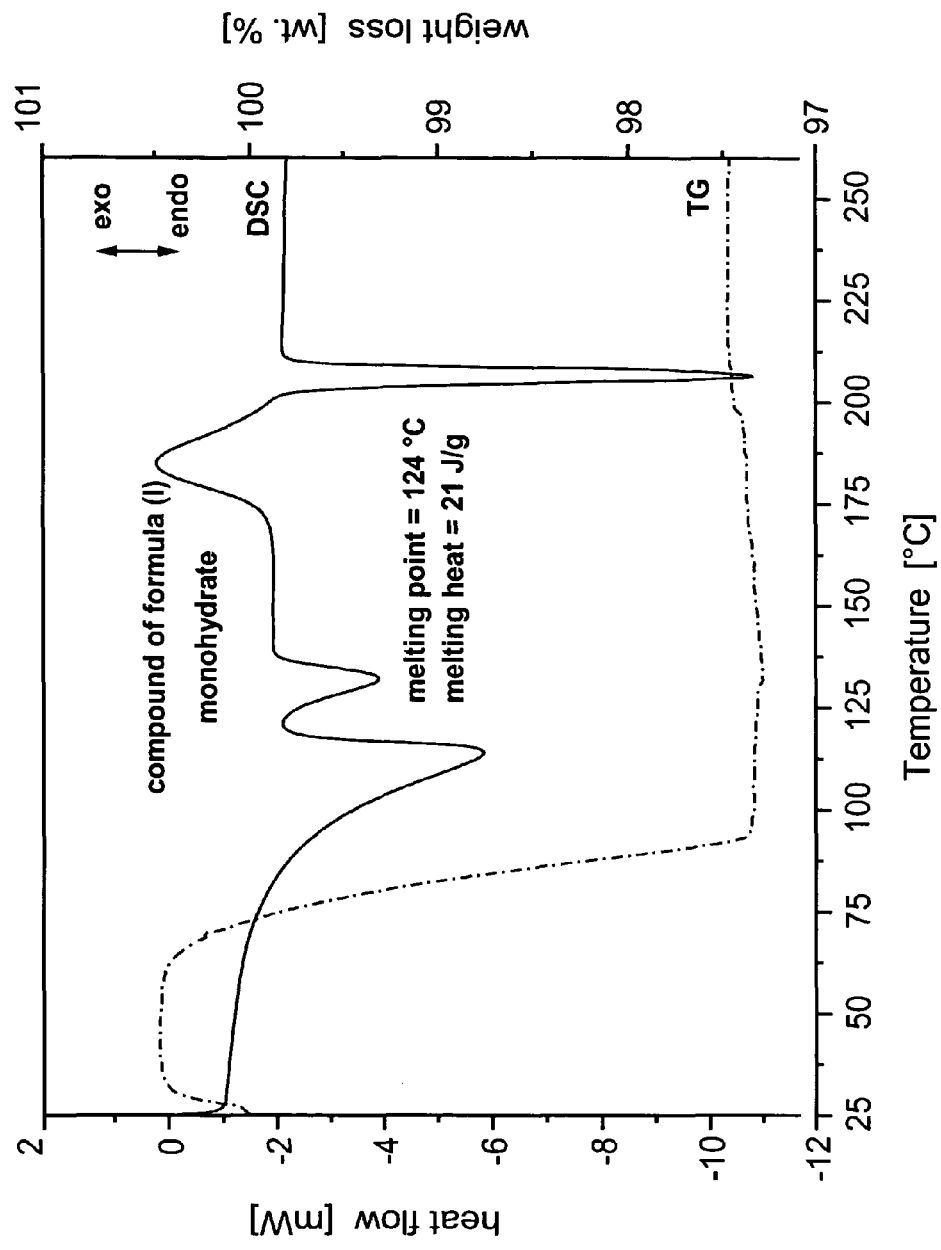
FIG. 1a: Compound of the formula (I) monohydrate characterized by DSC/TG (Differential Scanning Calorimetry/Thermogravimetry).

The present invention provides new hydrates and new polymorphic forms of the compound of formula (I) with an antiproliferative activity.

It therefore relates to hydrates of the compound of formula (I):

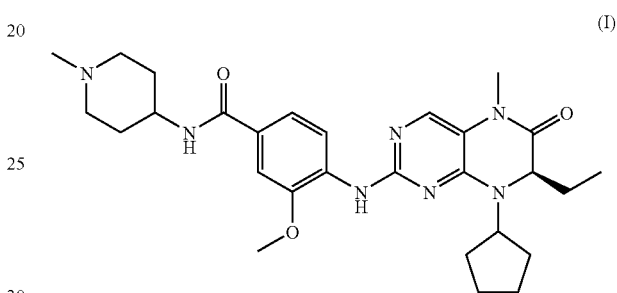

(I)

The hydrate of the compound of formula (I) is preferred, which is the monohydrate.

Also preferred is the hydrate of the compound of formula (I), which is the trihydrate.

The invention further relates to the anhydrate of the compound of formula (I).

Also preferred is the anhydrate of the compound of formula (I), which is present as the type I anhydrate.

Also preferred is the anhydrate of the compound of formula (I), which is present as the type II anhydrate.

Also preferred is the anhydrate of the compound of formula (I), which is present as the type III anhydrate.

The invention further relates to a pharmaceutical composition which contains a therapeutically effective amount of one of the hydrates and polymorphic forms of the compound of formula (I) according to the invention described above and one or more pharmaceutically acceptable excipients.

The invention further relates to the hydrates and polymorphic forms of the compound of formula (I) according to the invention for use as pharmaceutical compositions with an antiproliferative activity.

The invention further relates to the use of the hydrates and polymorphic forms of the compound of formula (I) according to the invention for preparing a pharmaceutical composition for the treatment and/or prevention of cancer, infections, inflammatory and autoimmune diseases.

The invention further relates to the use of the hydrates and polymorphic forms of the compound of formula (I) according to the invention for preparing a pharmaceutical composition for inhibiting polo-like kinases.

It is preferred according to the invention to use the hydrates and polymorphic forms of the compound of formula (I) for preparing a pharmaceutical composition for inhibiting the polo-like kinase PLK-1.

It is particularly preferred to use the hydrates and polymorphic forms of the compound of formula (I) according to the invention, the active substance being administered orally, enterally, intravenously, peritoneally or by injection.

The invention further relates to a process for preparing the compound of formula (I), characterised in that a compound of formula 4

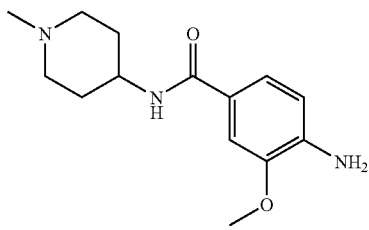

is reacted with a compound of formula 9,

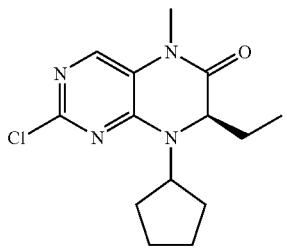

The invention further relates to a process for preparing a compound of formula 9,

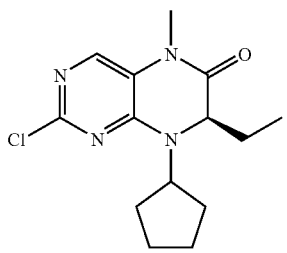

by methylation with dimethylcarbonate in the presence of a base at elevated temperature (between 80° C. and 180° C.), preferably at 130° C.

The invention further relates to a compound of formula 3

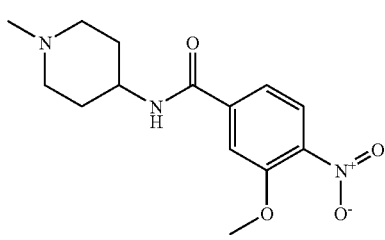

The invention further relates to compound of formula 4

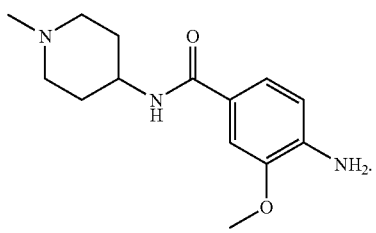

The invention further relates to a process for preparing the monohydrate of the compound of formula (I), which comprises the following steps:
(a) preparing a solution of the compound of formula (I), in a solvent mixture of isopropanol/water or acetone/water.
(b) crystallising the monohydrate of the compound of formula (I) from the solvent mixture
(c) isolating the monohydrate of the compound of formula (I).

The invention further relates to a process for preparing the trihydrate of the compound of formula (I), whereby the monohydrate of the compound of formula (I) is subjected to a relative humidity of at least 70%.

The invention further relates to a process for preparing the type III anhydrate of the compound of formula (I), wherein:
(a) The monohydrate of the compound of formula (I) is rinsed with dry nitrogen, or
(b) The monohydrate of the compound of formula (I) is subjected to a temperature of about 70° C., preferably 70 to 120° C., particularly preferably 70 to 90° C.

The invention further relates to a process for preparing the type I anhydrate of the compound of formula (I), whereby the type III anhydrate of the compound of formula (I) is melted and then the melt is crystallised at a temperature of at least 140° C., preferably from 140° C. to 160° C.

The invention further relates to a process for preparing the type I anhydrate of the compound of formula (I) comprising the following steps:
a) preparing a solution of the compound of formula (I) in a solvent mixture of ethyl acetate and methyl-tert.-butylether, preferably in the ratio ethyl acetate/methyl-tert.-butylether of 3:5 (v/v) or a solvent mixture of methylisobutylketone/cyclohexane.
b) crystallising the type I anhydrate of the compound of formula (I) from the solvent mixture and
c) isolating the type I anhydrate of the compound of formula (I).

The invention further relates to a process for preparing the type II anhydrate of the compound of formula (I) comprising the following steps:
a) preparing a solution of the compound of formula (I) in ethyl acetate,
b) crystallising the type II anhydrate of the compound of formula (I) from ethyl acetate followed by the addition of diethyl ether and
c) isolating the type II anhydrate of the compound of formula (I).

The invention further relates to a process for preparing the type I anhydrate of the compound of formula (I) comprising the following steps:
a) melting the type II anhydrate of the compound of formula (I),
b) crystallising the melt at a temperature of at least 185° C., preferably at a temperature of 185 to 200° C.

The compound of formula (I) may be prepared by the method of synthesis described hereinafter. The synthesis is shown in Diagram (1) and should be understood as illustrating the invention without restricting it to its contents.
Synthesis Plan 1
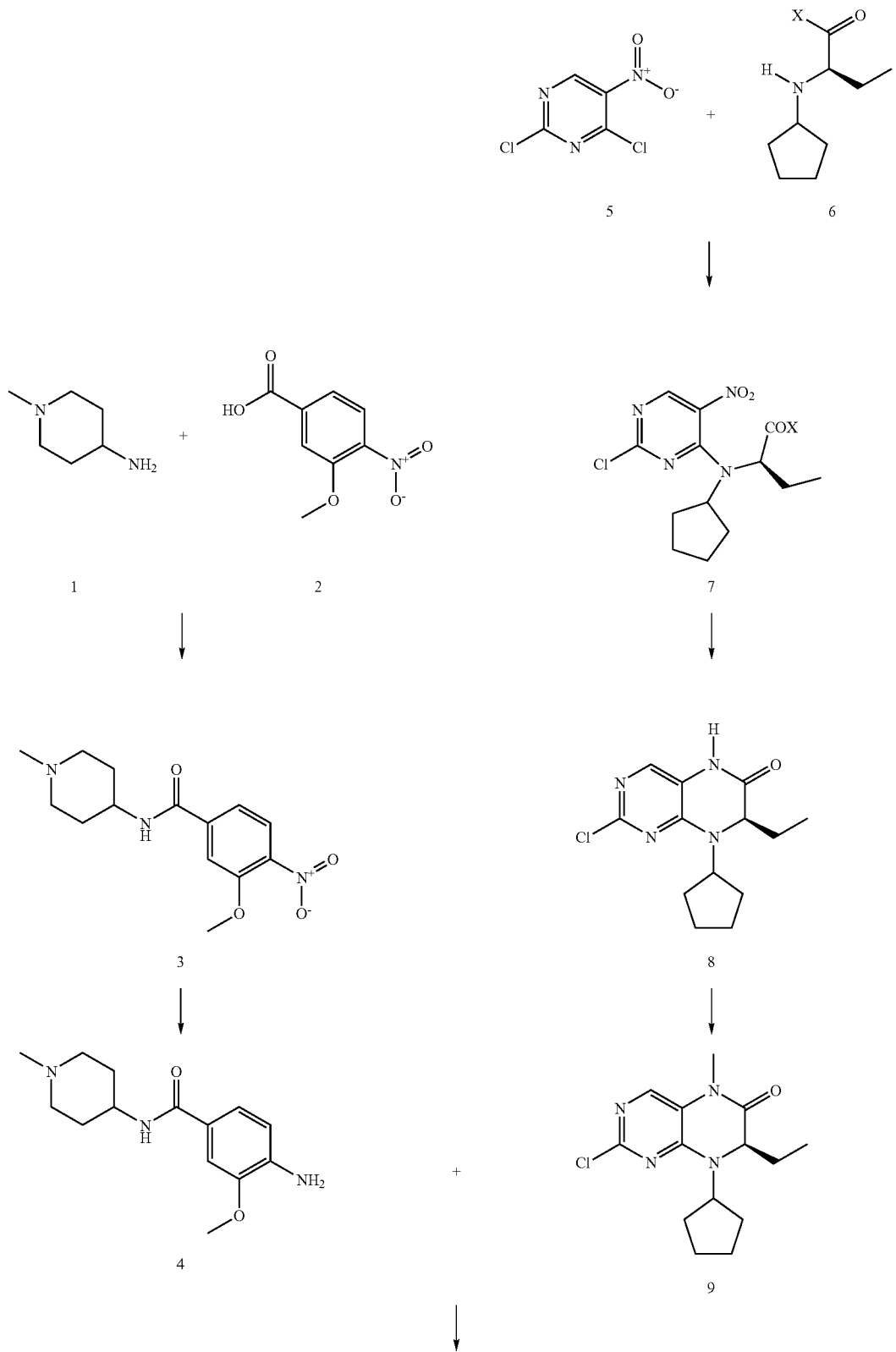

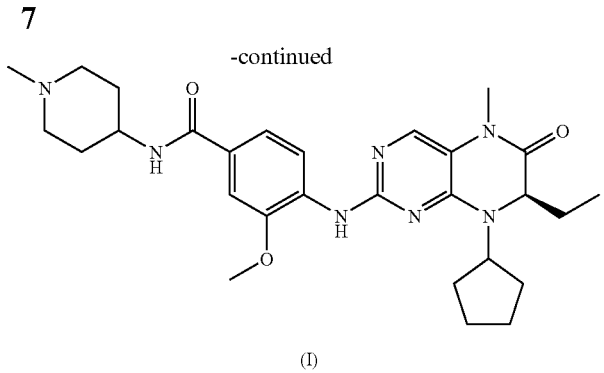

(I)

Preparation of the Aniline Fragment 4
Preparation of Compound 3

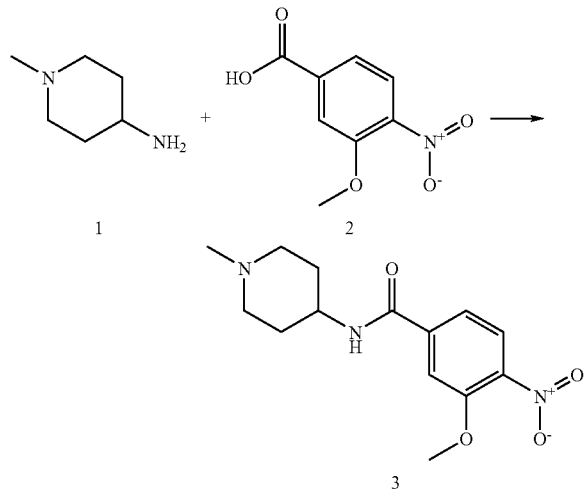

Variant 1A:

A suspension of 100 g (0.507 mol) of 3-methoxy-4-nitrobenzoic acid 2, 163 g (0.508 mol) O-(benzotriazol-1-yl)-N,N,N',N'-tetramethyluronium tetrafluoroborate and 192 mL (1.1 mol) ethyldiisopropylamine in 1.2 L dichloromethane is stirred for one hour at 25° C. 58 g (0.508 mol) 1-methyl-4-aminopiperidine 1 are added to the resulting solution and the mixture is stirred for 16 hours at 20° C. The solution is evaporated down to 600 mL and the organic phase is washed five times with 80 mL of 1 molar ammonia solution. The organic phase is concentrated by evaporation and the residue is chromatographed on silica gel using dichloromethane/methanol/conc. ammonia (15:1:0.1). Product fractions are combined, the solvent is evaporated off and the product is crystallised from ethyl acetate/methanol. 123 g of product 3 are obtained.

Variant 1B:

4.00 kg (20.3 mol) 3-methoxy-4-nitrobenzoic acid 2 are placed in 54 L toluene. 16 L toluene are distilled off under normal pressure. The mixture is cooled to 105° C. and 40 ml of dimethylformamide in 2 L toluene are added. At a jacket temperature of 120° C., 2.90 kg (24.3 mol) thionyl chloride are allowed to flow in within 30 min. and the mixture is rinsed with 4 L toluene. The reaction mixture is stirred for 1 hour at reflux temperature. Then 12 L toluene are distilled off under normal pressure. The contents of the reactor are cooled. A solution of 2.55 kg (22.3 mol) 1-methyl-4-aminopiperidine 1 in 2 L toluene and 2.46 kg (24.3 mol) triethylamine in 2 L toluene are allowed to flow in at 55-65° C. The mixture is rinsed with 4 L toluene. The suspension is stirred for 1 hour. 20 L of water are allowed to flow in and 3.08 kg (30.4 mol) conc. hydrochloric acid (36%) are added at 35-40° C. The mixture is rinsed with 2 L water. At 35-40° C. two phases are formed. The organic phase is separated off and the aqueous phase containing the product is returned to the reactor. It is rinsed with 4 L water. Under reduced pressure 3.2 L water are distilled off at 50° C. 4.87 kg (60.9 mol) sodium hydroxide solution (50%) are added to the remaining solution at 40° C. The mixture is rinsed with 4 L water. The product suspension is allowed to cool to 22° C. and stirred for 30 min. at this temperature. The suspension is suction filtered and the filter cake is washed with 40 L water. The product is dried at 40° C. in the vacuum drying cupboard. 5.65 kg of product are obtained.

Preparation of the Compound 4:

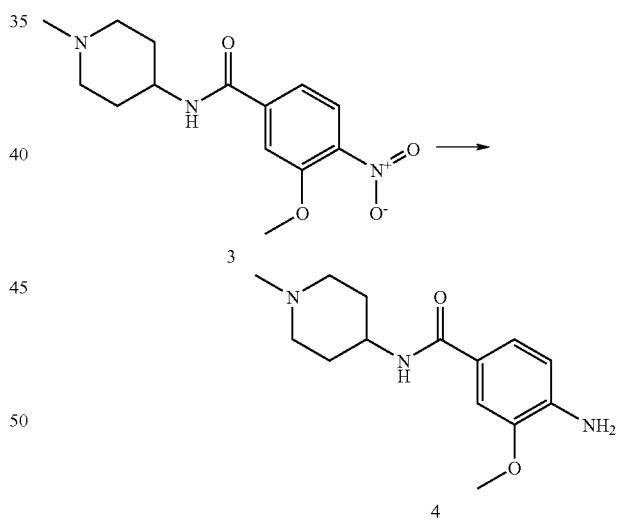

Variant 2A

A solution of 145 g (0.494 mol) 3 in 2 L methanol is hydrogenated at 4 bar in the presence of 2 g palladium on charcoal (10%). The catalyst is filtered off and the filtrate is concentrated by evaporation. 128 g product 4 are obtained.

Variant 2B

25 L demineralised water are added to 5.00 kg (17.0 mol) 3 and 600 g activated charcoal (industrial grade). Then 2.05 kg (34.1 mol) acetic acid are added. The suspension is stirred for 15 minutes at 22-25° C. 500 g of palladium on charcoal (10%) suspended in 3 L demineralised water are added and the mixture is rinsed with 2 L demineralised water. The contents of the reactor are heated to 40° C. and the mixture is hydrogenated at this temperature until the uptake of hydrogen ceases. The reaction mixture is filtered and the filter cake is washed with 10 L demineralised water.

For crystallisation the filtrate is transferred into a reactor and the transporting container is rinsed with 5 L demineralised water. The reactor contents are heated to 50° C. A mixture of 5.45 kg (68.2 mol) sodium hydroxide solution (50%, industrial grade) and 7 L demineralised water is added. The mixture is stirred for 10 minutes at 45-50° C. The suspension is cooled to 20° C. and stirred for 1-1.5 hours at this temperature. The product is suction filtered, washed with 30 L demineralised water and dried at 45° C. in the vacuum drying cupboard. 4.13 kg of product 4 are obtained.

Preparation of the Dihydropteridinone Fragment 9
Preparation of the Amino Acid Esters 6a-d

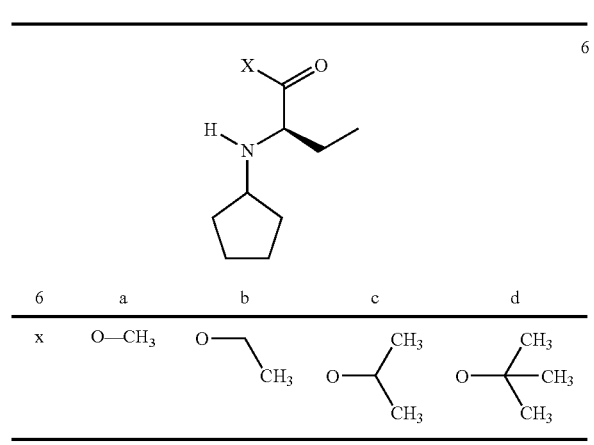

The methyl ester 6a, ethyl ester 6b and 2-propyl ester 6c are prepared by methods described in the literature, for example according to WO 03/020722. The tert.-butyl ester 6d is prepared by transesterification with tert.-butyl acetate in the presence of perchloric acid (J. Med. Chem., Vol 37, No 20, 1994, 3294-3302).

The amino acids may be used in the form of the bases or as hydrochlorides in the following nucleophilic substitution reaction.

Preparation of the Amino Acid Amides 6e,f

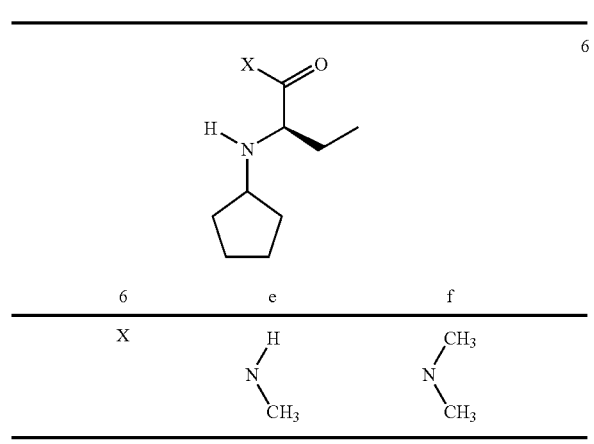

The amino acid amide 6e is prepared by aminolysis of the methyl ester 6a with 40% aqueous methylamine solution at ambient temperature.

The amino acid amide 6f is prepared by amide formation of the free amino acid with a five-fold excess of 2 molar dimethylamine solution in tetrahydrofuran in the presence of O-(benzotriazol-1-yl)-N,N,N',N'-tetramethyluronium tetrafluoroborate as coupling reagent.

Preparation of the Compounds 7

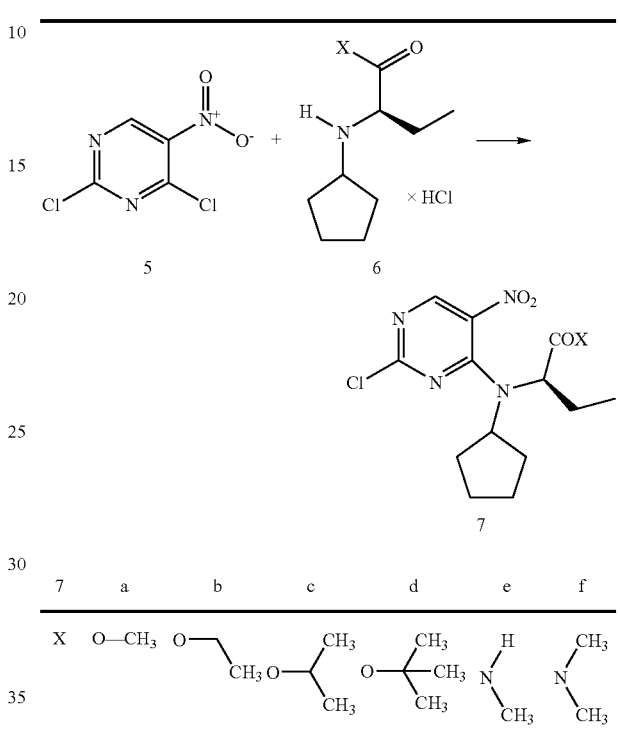

Preparation of the Methylester 7a

A suspension of 457 g (2.06 mol) of the amino acid methylester 6a and 693 g (8.25 mol) of powdered sodium hydrogen carbonate in 10 L cyclohexane is stirred for 15 minutes at ambient temperature. 440 g (2.27 mol) 2,4-dichloro-5-nitropyrimidine 5 and 1.5 L cyclohexane are added and the mixture is stirred for 3 days at ambient temperature. The reaction is monitored by HPLC. In order to redissolve any product which has crystallised out, 4 L of dichloromethane are added to the suspension. After the addition of 335 g magnesium sulphate the suspension is suction filtered and the inorganic filter cake is washed again with dichloromethane. The filtrate is evaporated down to 3.1 kg under reduced pressure and the suspension obtained is refluxed. The solution is allowed to cool slowly and stirred for one hour at 10-15° C. The suspension is suction filtered and the filter cake is washed with cyclohexane. The product is dried at 40° C. in the vacuum drying cupboard. 582 g of 7a (X=OCH$_3$) are obtained as a dark yellow solid.

Lipophilic solvents such as e.g. cyclohexane, methylcyclohexane, toluene and the mixtures thereof are particularly suitable for achieving high regioselectivity in the nucleophilic substitution in compound 5.

Compounds 7b-f are prepared analogously to this method. During the reaction of the amino acid amide 7e,f a fairly polar solvent such as e.g. ethyl acetate or dichloromethane is added to improve solubility.

Preparation of Compound 8

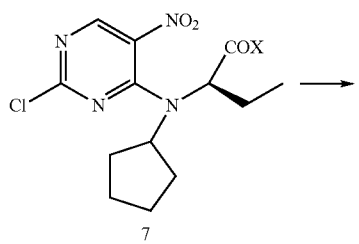

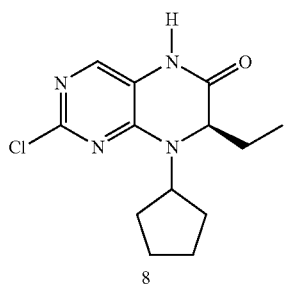

A freshly prepared suspension of 560 g (1.63 mol) 7a and 185 g Raney nickel in 2.8 L acetic acid is hydrogenated at 75° C. After the uptake of hydrogen has ended the catalyst is filtered off and the hydrogenation solution is evaporated down under reduced pressure. 4 L of demineralised water and 4 L ethyl acetate are added to the residue. A precipitate which contains the product is formed between the phases. The aqueous phase is separated off. 2 L ethyl acetate are added to the organic phase and the precipitate is suction filtered. The precipitate is suspended in 600 mL demineralised water, stirred for 1 hour at ambient temperature, suction filtered and washed with demineralised water. 110 g of moist product A are obtained.

The filtrate is washed three times with sodium chloride solution. The organic phase is concentrated by evaporation. 380 g of a reddish-brown residue B are obtained, which is combined with the moist product A. The combined crude products A and B are dissolved in 1.5 L ethanol at reflux temperature. The solution is filtered clear and the filter is rinsed with 150 mL ethanol. 550 mL demineralised water are added to the solution at reflux temperature. The mixture is left to cool and stirred for 16 hours at ambient temperature and for 3 hours at 0-5° C. The precipitate is suction filtered and washed with demineralised water/methanol (1:1) and then with demineralised water. The product is dried at 50° C. in the vacuum drying cupboard. 266 g product 8 are obtained as a solid.

Preparation of Compound 9 (Variant 3A)

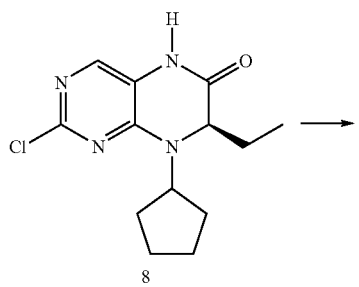

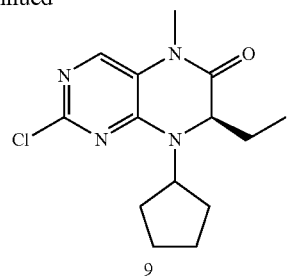

38 g (0.95 mol) sodium hydride (60% dispersion in mineral oil) are added batchwise to a solution of 264 g (0.94 mol) of 8 and 161 g (1.13 mol) methyl iodide in 2 L dimethylacetamide at 4-10° C. within one hour. The cooling bath is removed and the mixture is allowed to come up to 20° C. within 2 hours. It is cooled to 10° C. and a further 0.38 g (9.5 mmol) sodium hydride are added. The mixture is stirred for 4 hours at 10-15° C. 100 mL ethyl acetate and 1 kg ice are added to the reaction solution. The resulting suspension is diluted with 3 L demineralised water. The suspension is stirred for 2 hours, the precipitate is suction filtered and the filter cake is washed with demineralised water. The product is dried at 50° C. in the vacuum drying cupboard. 273 g of product 9 are obtained as colourless crystals.

Preparation of Compound 9 (Variant 3B)

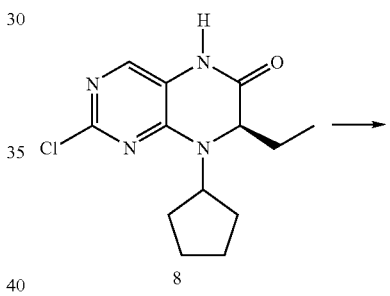

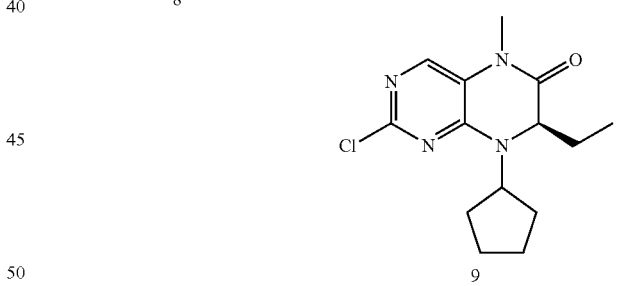

A suspension of 100 g (356 mmol) 8 and 73.8 g (534 mmol) potassium carbonate in 400 mL dimethylcarbonate is heated to 130° C. in an autoclave for 6 hours. The mixture is left to cool and 300 mL demineralised water and 200 mL ethyl acetate are added with stirring. The aqueous phase is separated off together with undissolved salts. 500 mL of solvent are distilled off from the organic phase at a pressure 180 mbar and a heating bath temperature of 70° C. 600 mL demineralised water are added to the residue and 100 mL solvent are distilled off at a pressure of 150 mbar and a heating bath temperature of 80° C. 350 mL ethanol are added to the suspension which is then heated to 65° C. The solution is left to cool and inoculated. It is cooled to 10° C., the precipitate is suction filtered and washed with a mixture of demineralised water and ethanol (2.5:1). The product is dried at 50° C. in the vacuum drying cupboard. 95.5 g product 9 are obtained.

Preparation of Compound of Formula (I)

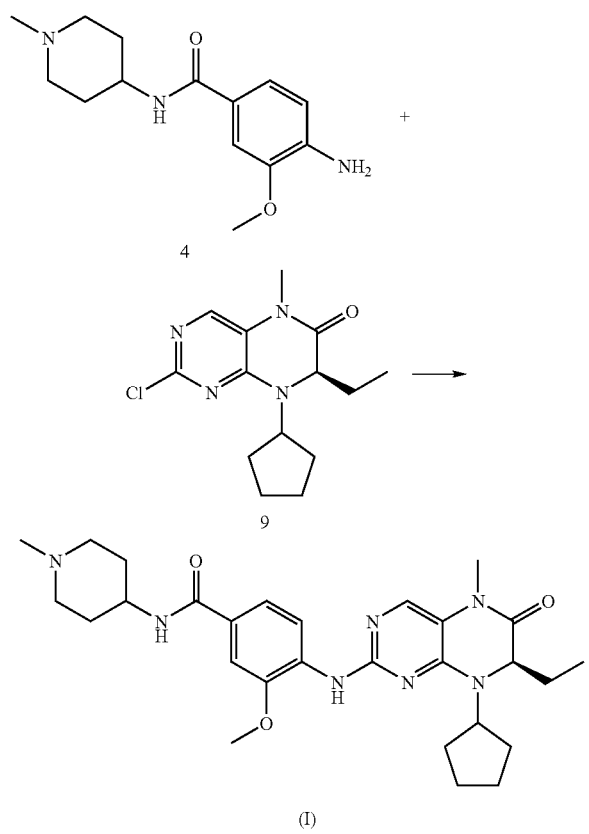

A suspension of 201 g (1.06 mol) para-toluenesulphonic acid-hydrate, 209 g (706 mmol) 9 and 183 g (695 mmol) 4 in 800 mL 2-methyl-4-pentanol is refluxed. 100 mL solvent are distilled off. The mixture is refluxed for 3 hours, 200 mL of 2-methyl-4-pentanol are added and 120 mL of solvent are distilled off. After 2 hours heating at reflux temperature a further 280 mL solvent are distilled off. The mixture is cooled to 100° C. and 1 L demineralised water and then 0.5 L ethyl acetate are added to the reaction solution. The organic phase is separated off and the aqueous phase is again washed with 0.5 L ethyl acetate. 1.5 L dichloromethane and 0.5 L ethyl acetate are added to the acidic aqueous phase. The pH value of the aqueous phase is adjusted to pH 9.2 with 260 mL of 6 normal sodium hydroxide solution. The aqueous phase is separated off and the organic phase is washed three times with in each case 1 L of 1 normal aqueous sodium hydrogen carbonate solution. The organic phase is dried over sodium sulphate, filtered and the solvent is evaporated down under reduced pressure. 406 g crude product are obtained.

The crude product is dissolved in 1.5 L ethyl acetate. At a temperature of 50-55° C. 2.5 L of methyl-tert.-butylether are added. The mixture is inoculated at 45° C. and stirred for 16 hours with cooling to ambient temperature. The suspension is stirred for 3.5 hours at 0-5° C. and the precipitate is suction filtered. The filter cake is washed again with methyl-tert.-butylether/ethyl acetate (2:1) and methyl-tert.-butylether. The product is dried at 50° C. in the vacuum drying cupboard. 236 g of crystalline product of the compound of formula (I) are obtained as the type I anhydrate.
Crystallisation:

46.5 g of the crystalline type I anhydrate described above are dissolved in 310 mL 1-propanol and filtered clear. The mixture is heated to 70° C. and 620 mL demineralised water are added. The solution is left cool to ambient temperature, cooled to 0-10° C. and seed crystals are added. The resulting suspension is stirred for 3 hours at 0-10° C. It is suction filtered and washed with cold 1-propanol/demineralised water (1:2) and demineralised water. The product is dried at 50° C. in the vacuum drying cupboard. 40.5 g crystalline product of the compound of formula (I) are obtained as the monohydrate.

The crude product of the reaction described above may also be crystallised directly as the crystalline monohydrate from 1-propanol/demineralised water.

The preparation of the hydrates and anhydrates of the compound of formula (I) may be carried out according to the following methods. These methods are shown in Diagram 2 and should be understood as illustrating the invention without restricting it to their content.

Polymorphous Characteristics of the Compound of Formula (I)

Figure 1B:
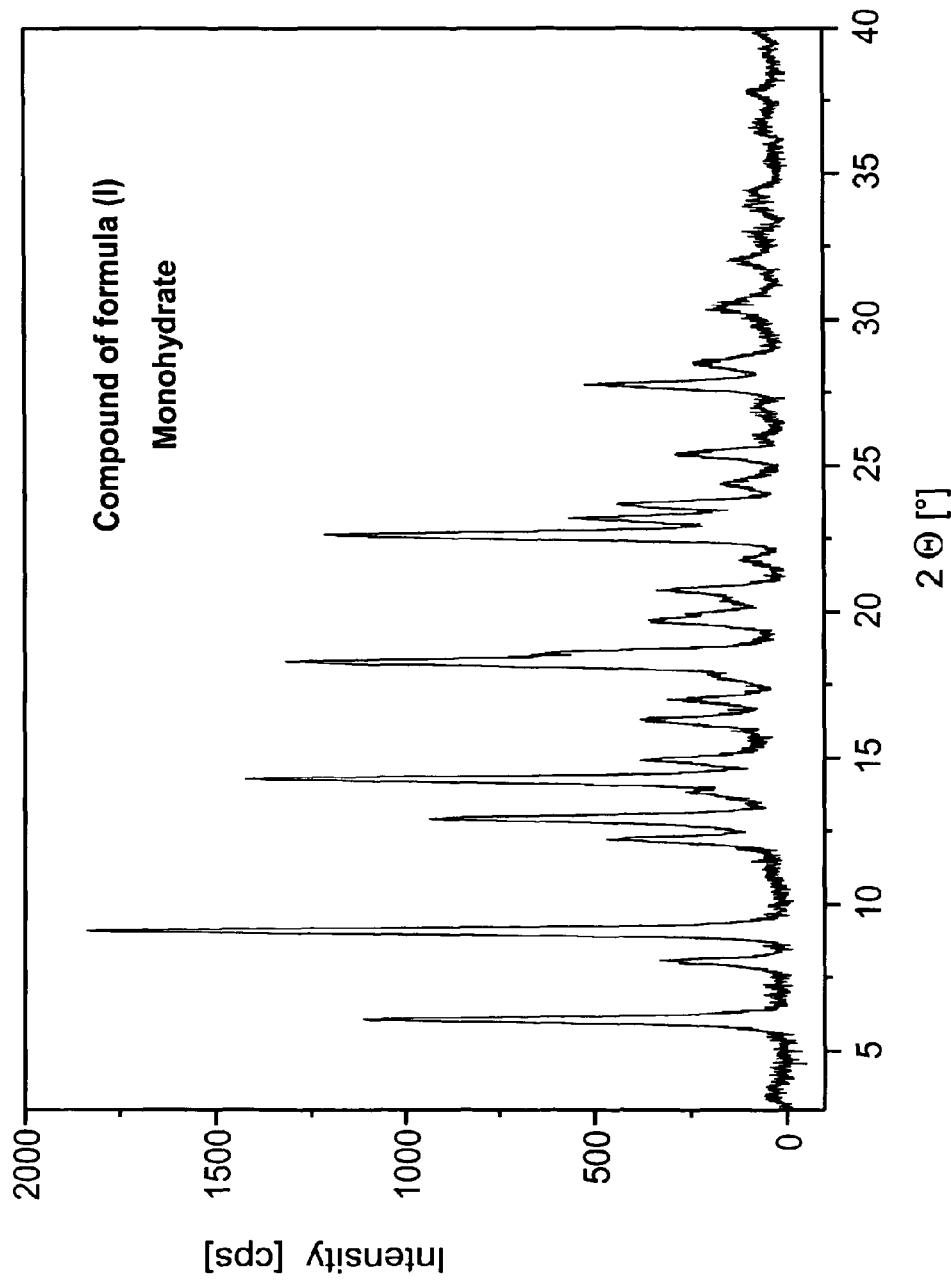
FIG. 1b: Compound of the formula (I) monohydrate characterized by X-ray powder diffraction.
Figure 2A:
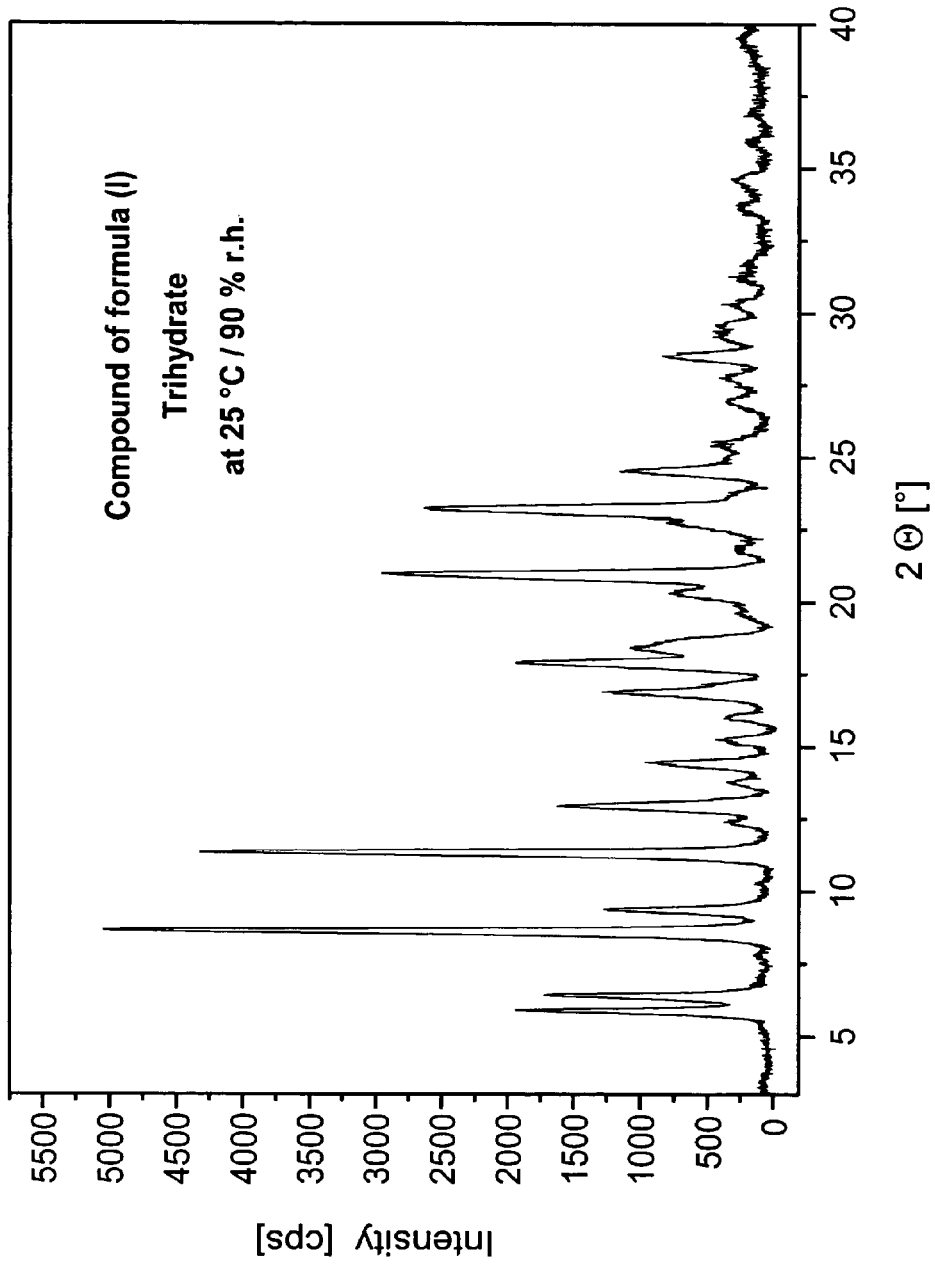
FIG. 2a: Compound of formula (I) Trihydrate characterized by X-ray powder diffraction.
Figure 3A:
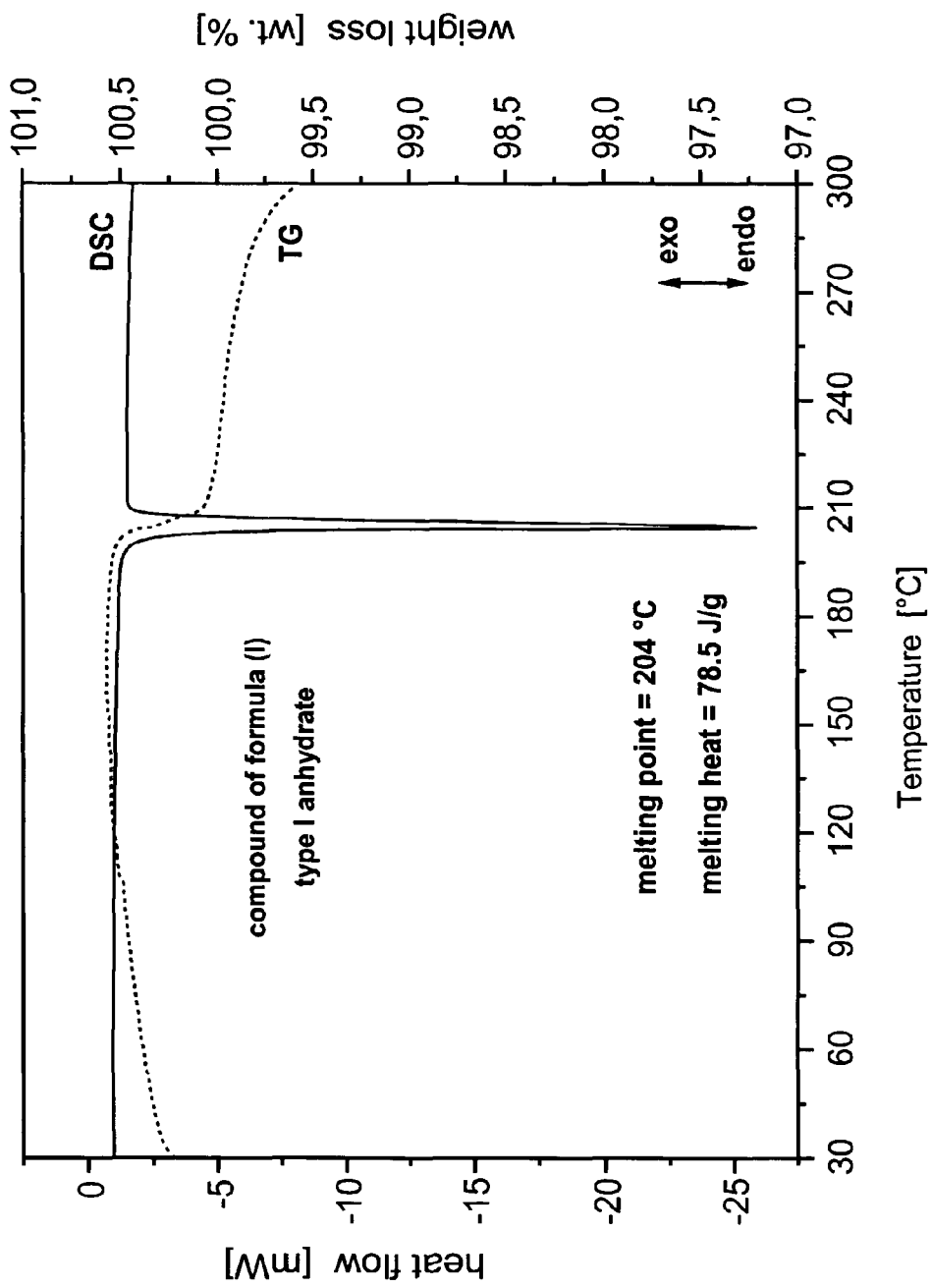
FIG. 3a: Compound of formula (I) type I anhydrate characterized by DSC/TG (Differential Scanning Calorimetry/Thermogravimetry).
Figure 3B:
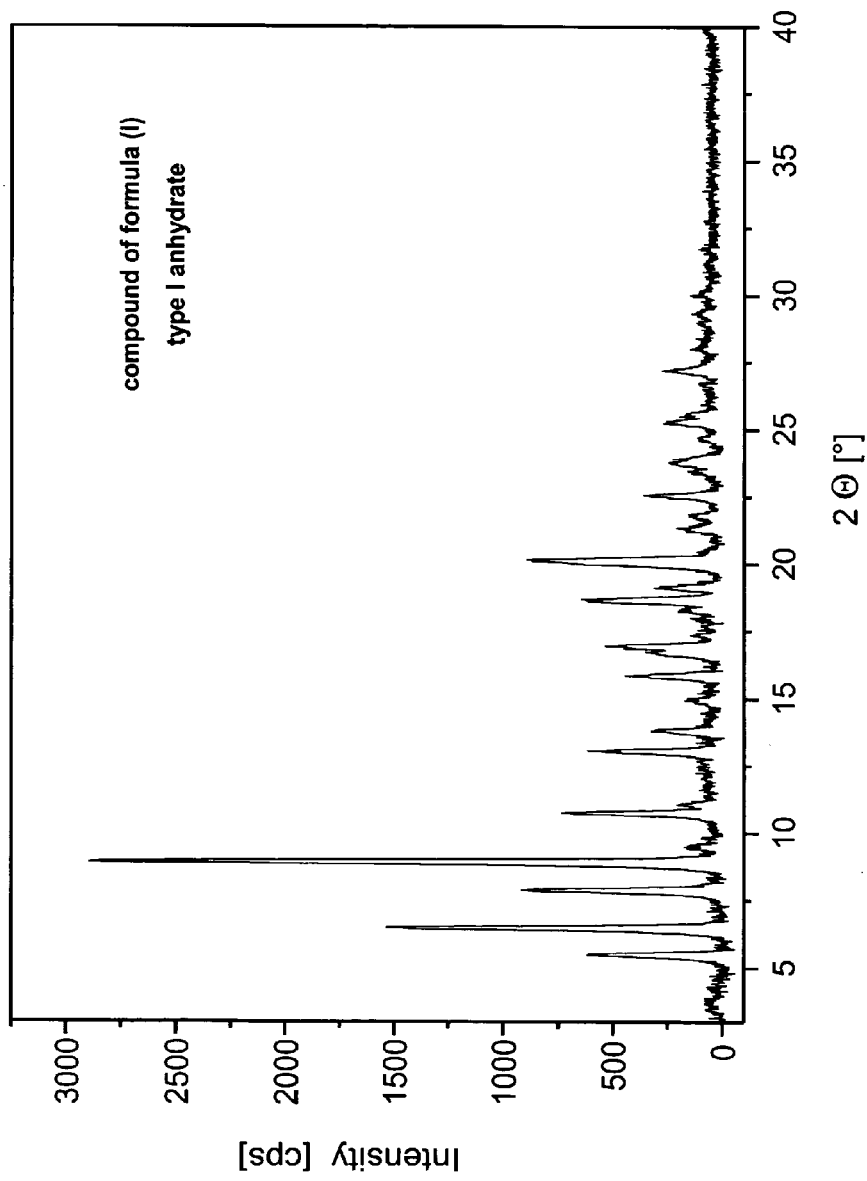
FIG. 3b: compound of formula (I) type I anhydrate characterized by X-ray powder diffraction.
Figure 4A:
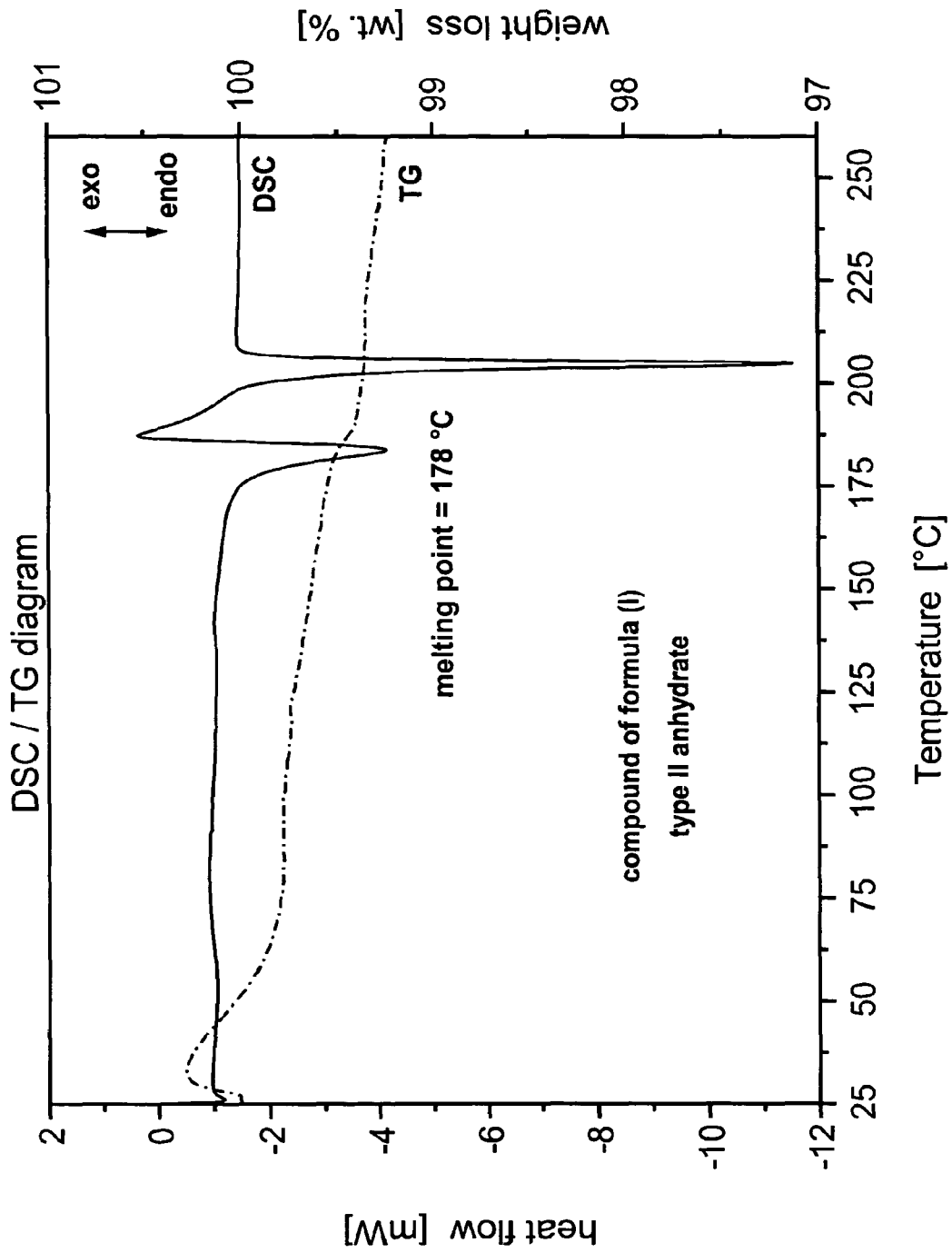
FIG. 4a: Compound of formula (I) type II anhydrate characterized by DSC/TG (Differential Scanning Calorimetry/Thermogravimetry).
Figure 4B:
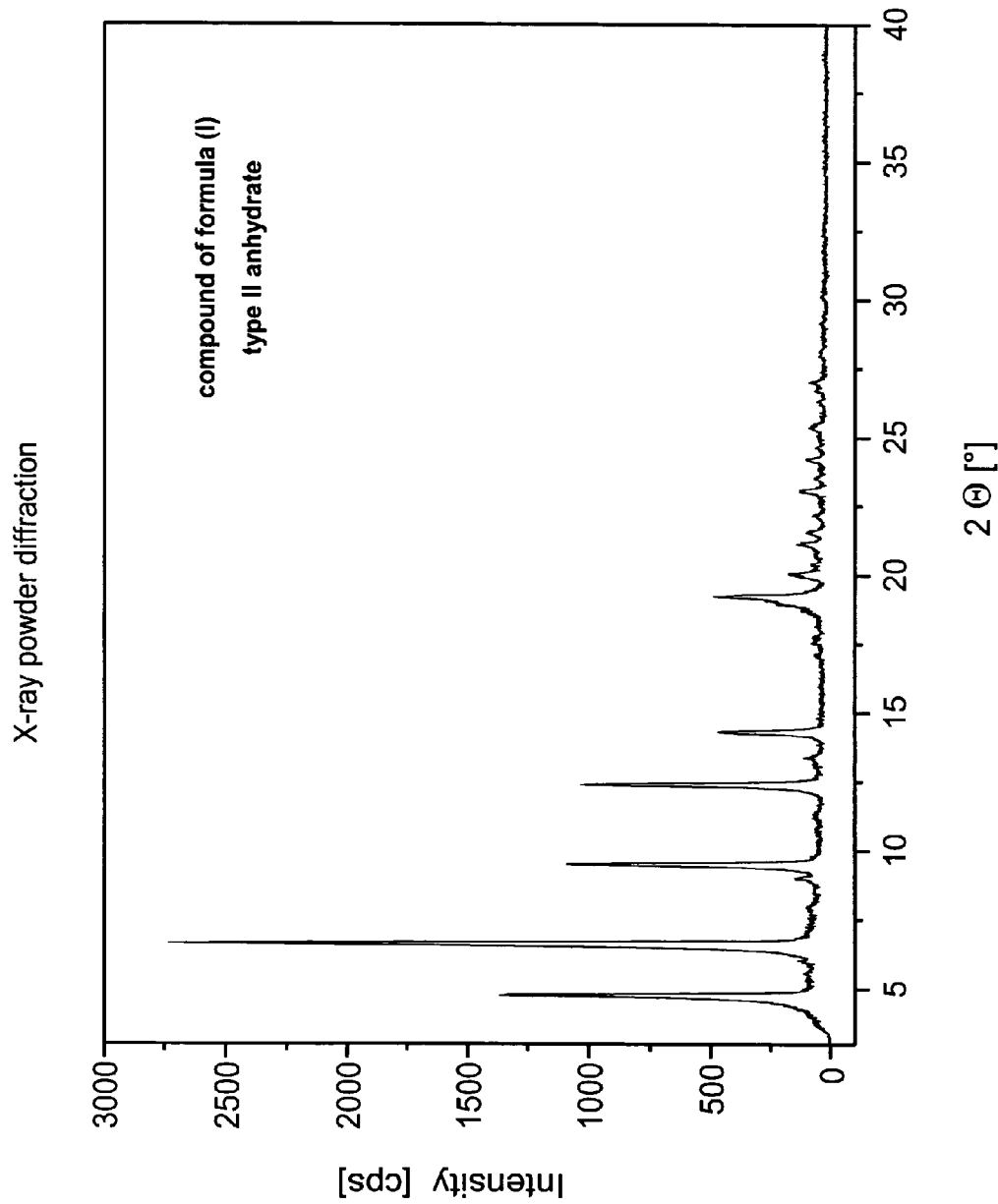
FIG. 4b: Compound of formula (I) type II anhydrate characterized by X-ray powder diffraction.
Figure 5A:
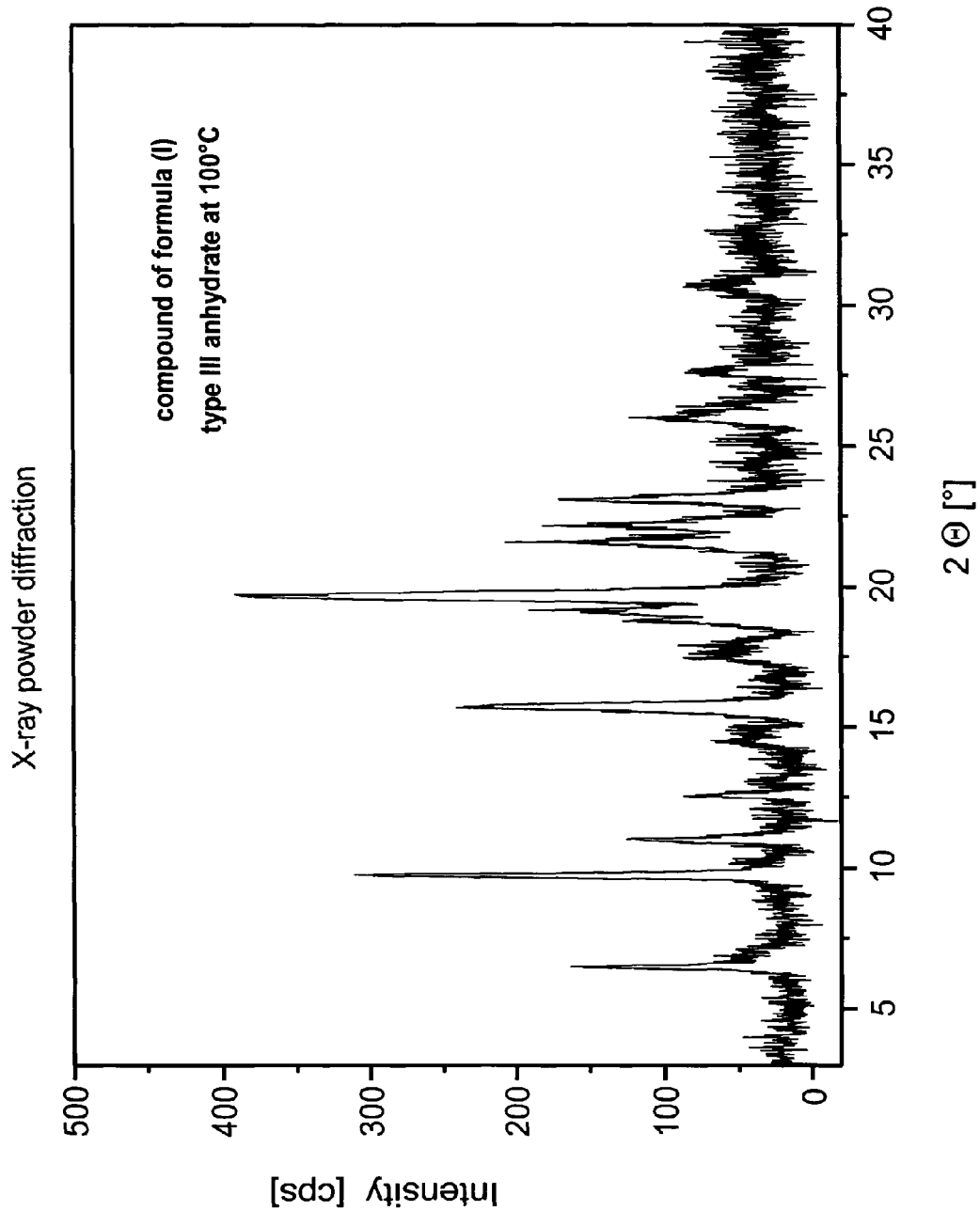
FIG. 5a: Compound of formula (I) type III anhydrate characterized by X-ray powder diffraction.
Figure 6A:
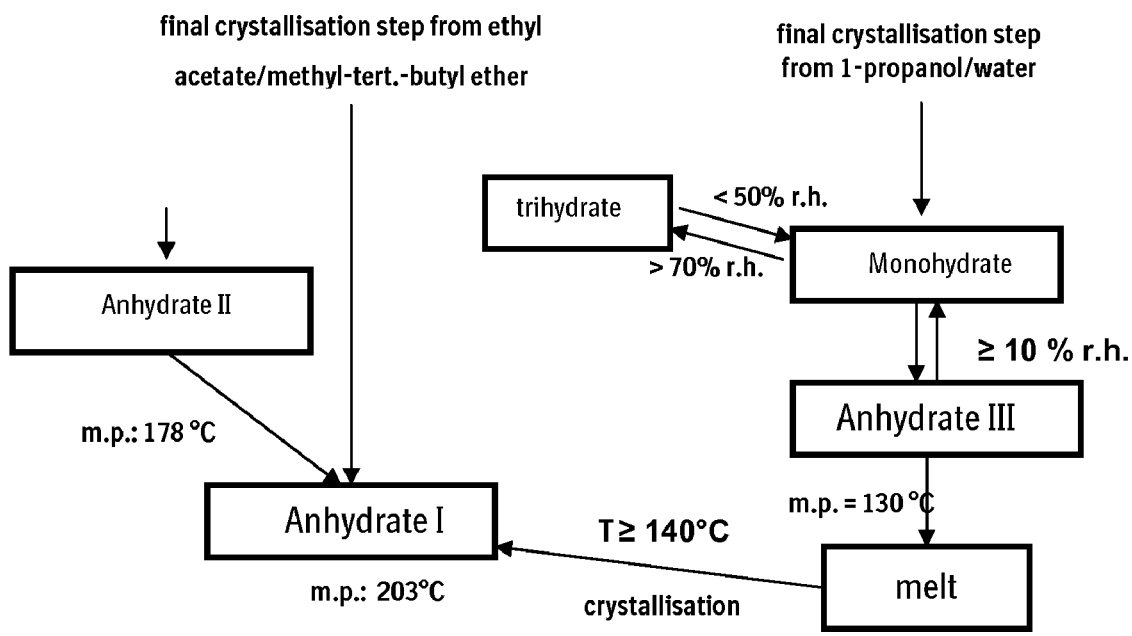
FIG. 6a: Methods showing the preparation of the hydrates and anhydrates of the compound of formula (I).

The hydrates and anhydrates according to the invention are characterised by DSC/TG (Differential Scanning Calorimetry/Thermogravimetry) and XRD (X-ray powder diffractograms) (Tables 1-5, FIGS. 1a to 5a).

All the XRD powder diffractograms were obtained using methods known in the art, by means of an X-ray powder diffractometer (Bruker D8 Advance). The diffractograms were obtained under the following measuring conditions: CuKα radiation ($\lambda$=1.5418 Å), 40 kV, 40 mA.

The DSC/TG measurements were carried out using equipment produced by the company Mettler Toledo (DSC 821 and TGA 851). The samples used were between 2 and 10 mg for DSC measurements and 10-30 mg for TG measurements. The heating rates were 10 K/min, and the measurements were carried out under an inert atmosphere (nitrogen flushing).

TABLE 1

X-ray powder reflections and their intensities (standardised) under normal ambient conditions of the monohydrate of the compound of formula (I)

| 2 Θ [°] | $d_{hkl}$ [Å] | intensity $I/I_o$ [%] |
|---|---|---|
| 6.07 | 14.54 | 62 |
| 8.06 | 10.96 | 15 |
| 9.11 | 9.7 | 100 |
| 12.23 | 7.23 | 24 |
| 12.93 | 6.84 | 50 |
| 13.81 | 6.41 | 13 |
| 14.29 | 6.2 | 76 |
| 14.94 | 5.92 | 18 |
| 16.29 | 5.44 | 18 |
| 17.01 | 5.21 | 15 |
| 17.8 | 4.98 | 8 |
| 18.29 | 4.85 | 69 |
| 18.6 | 4.77 | 32 |
| 19.71 | 4.5 | 18 |
| 19.94 | 4.45 | 13 |
| 20.43 | 4.34 | 7 |
| 20.76 | 4.27 | 17 |
| 21.8 | 4.07 | 5 |
| 22.64 | 3.92 | 65 |
| 23.21 | 3.83 | 29 |
| 23.67 | 3.76 | 22 |
| 24.38 | 3.65 | 7 |
| 25.4 | 3.5 | 14 |
| 25.98 | 3.43 | 2 |
| 27.01 | 3.3 | 3 |
| 27.78 | 3.21 | 27 |
| 28.49 | 3.13 | 11 |
| 30.41 | 2.94 | 9 |

TABLE 2

X-ray powder reflections and their intensities (standardised) at ambient temperature and 90% r.h. of the trihydrate of the compound of formula (I)

| 2 Θ [°] | $d_{hkl}$ [Å] | intensity $I/I_o$ [%] |
|---|---|---|
| 5.93 | 14.89 | 39 |
| 6.45 | 13.68 | 34 |
| 8.69 | 10.17 | 100 |
| 9.45 | 9.35 | 26 |
| 11.43 | 7.74 | 85 |
| 12.5 | 7.08 | 8 |
| 13.06 | 6.77 | 32 |
| 13.89 | 6.37 | 7 |
| 14.57 | 6.08 | 19 |
| 15.38 | 5.76 | 9 |
| 16.18 | 5.47 | 7 |
| 17.04 | 5.2 | 25 |
| 17.34 | 5.11 | 10 |
| 18.07 | 4.91 | 37 |
| 18.59 | 4.77 | 21 |
| 18.85 | 4.71 | 16 |
| 19.81 | 4.48 | 5 |
| 20.52 | 4.32 | 15 |
| 21.18 | 4.19 | 57 |
| 22.06 | 4.03 | 5 |
| 22.96 | 3.87 | 15 |
| 23.46 | 3.79 | 51 |
| 24.79 | 3.59 | 21 |
| 25.74 | 3.46 | 7 |
| 27.23 | 3.27 | 6 |
| 28.04 | 3.18 | 7 |
| 28.8 | 3.1 | 15 |
| 29.52 | 3.02 | 7 |
| 29.88 | 2.99 | 7 |
| 30.58 | 2.92 | 5 |

TABLE 3

X-ray powder reflections and their intensities (standardised) under normal ambient conditions of the anhydrate I of the compound of formula (I)

| 2 Θ [°] | $d_{hkl}$ [Å] | intensity $I/I_o$ [%] |
|---|---|---|
| 5.48 | 16.11 | 22 |
| 6.47 | 13.65 | 51 |
| 7.88 | 11.21 | 31 |
| 8.93 | 9.89 | 100 |
| 9.5 | 9.31 | 5 |
| 10.74 | 8.23 | 22 |
| 11.06 | 7.99 | 5 |
| 13.06 | 6.78 | 19 |
| 13.81 | 6.41 | 9 |
| 14.95 | 5.92 | 4 |
| 15.86 | 5.58 | 14 |
| 16.71 | 5.3 | 10 |
| 16.94 | 5.23 | 17 |
| 18.27 | 4.85 | 5 |
| 18.65 | 4.75 | 20 |
| 19.14 | 4.63 | 9 |
| 20.12 | 4.41 | 29 |
| 21.32 | 4.16 | 5 |
| 21.81 | 4.07 | 4 |
| 22.57 | 3.94 | 11 |
| 23.44 | 3.79 | 4 |
| 23.78 | 3.74 | 7 |
| 24.66 | 3.61 | 3 |
| 25.28 | 3.52 | 7 |
| 25.55 | 3.48 | 4 |
| 27.21 | 3.27 | 8 |
| 28.03 | 3.18 | 2 |
| 29.35 | 3.04 | 3 |
| 30.04 | 2.97 | 3 |

TABLE 4

X-ray powder reflections and their intensities (standardised) under normal ambient conditions of the anhydrate II of the compound of formula (I)

| 2 Θ [°] | $d_{hkl}$ [Å] | intensity $I/I_o$ [%] |
|---|---|---|
| 4.76 | 18.55 | 50 |
| 6.64 | 13.3 | 100 |
| 7.92 | 11.15 | 1 |
| 9.03 | 9.79 | 3 |
| 9.51 | 9.29 | 39 |
| 11.29 | 7.83 | 1 |
| 12.39 | 7.14 | 37 |
| 13.41 | 6.6 | 2 |
| 14.31 | 6.18 | 16 |
| 17.1 | 5.18 | 1 |
| 17.58 | 5.04 | 1 |
| 18.72 | 4.74 | 3 |
| 19 | 4.67 | 7 |
| 19.23 | 4.61 | 17 |
| 20.04 | 4.43 | 5 |
| 20.39 | 4.35 | 2 |
| 21.15 | 4.2 | 4 |
| 21.57 | 4.12 | 2 |
| 22.18 | 4 | 1 |
| 23.07 | 3.85 | 4 |
| 23.54 | 3.78 | 1 |
| 24.2 | 3.67 | 3 |
| 24.65 | 3.61 | 1 |
| 25.37 | 3.51 | 2 |
| 26.28 | 3.39 | 1 |
| 26.74 | 3.33 | 1 |
| 27.01 | 3.3 | 2 |
| 27.95 | 3.19 | 1 |
| 28.13 | 3.17 | 1 |

TABLE 5

X-ray powder reflections and their intensities (standardised) at 100° C. of the type III anhydrate of the compound of formula (I)

| 2 Θ [°] | $d_{hkl}$ [Å] | intensity $I/I_o$ [%] |
|---|---|---|
| 6.49 | 13.61 | 41 |
| 9.74 | 9.07 | 81 |
| 10.99 | 8.04 | 29 |
| 12.56 | 7.04 | 21 |
| 14.44 | 6.13 | 13 |
| 14.95 | 5.92 | 8 |
| 15.72 | 5.63 | 59 |
| 17.5 | 5.06 | 14 |
| 17.89 | 4.95 | 11 |
| 18.8 | 4.72 | 29 |
| 19.14 | 4.63 | 46 |
| 19.68 | 4.51 | 100 |
| 21.58 | 4.12 | 50 |
| 22.19 | 4 | 43 |
| 23.09 | 3.85 | 40 |
| 25.99 | 3.43 | 29 |
| 27.66 | 3.22 | 17 |
| 30.74 | 2.91 | 12 |

The anhydrate I, anhydrate II and monohydrate of the compound of formula (I) according to the invention may be used on their own or in conjunction with other active substances according to the invention, optionally also in conjunction with other pharmacologically active substances.

Suitable preparations include for example tablets, capsules, suppositories, solutions,—particularly solutions for injection (s.c., i.v., i.m.) and infusion—elixirs, emulsions or dispersible powders. The proportion of the pharmaceutically active compound(s) should be in the range from 0.01 to 90 wt.-%, preferably 0.1 to 50 wt.-% of the composition as a whole, i.e. in amounts which are sufficient to achieve the dosage range specified below. If necessary the doses specified may be given several times a day.

Suitable tablets may be obtained, for example, by mixing the active substance(s) with known excipients, for example inert diluents such as calcium carbonate, calcium phosphate or lactose, disintegrants such as maize starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral route, by injection or transdermally. For oral administration the tablets may of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used. The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The following examples of formulations illustrate the present invention without restricting its scope:

Examples of Pharmaceutical Formulations

| A) Tablets | per tablet |
|---|---|
| active substance | 100 mg |
| lactose | 140 mg |
| maize starch | 240 mg |
| polyvinylpyrrolidone | 15 mg |
| magnesium stearate | 5 mg |
| | 500 mg |

The finely ground active substance, lactose and some of the maize starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| lactose | 55 mg |
| maize starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the maize starch, lactose, microcrystalline cellulose and polyvinylpyrrolidone are mixed together, the mixture is screened and worked with the remaining maize starch and water to form a granulate which is dried and screened. The sodium carboxymethyl starch and the magnesium stearate are added and mixed in and the mixture is compressed to form tablets of a suitable size.

| C) Ampoule solution | |
|---|---|
| active substance | 50 mg |
| sodium chloride | 50 mg |
| water for inj. | 5 ml |

The active substance is dissolved in water at its own pH or optionally at pH 3.5 to 6.5 and sodium chloride is added to make the solution isotonic. The resulting solution is filtered to remove pyrogens and the filtrate is transferred under aseptic conditions into ampoules which are then sterilised and heat-sealed. The ampoules contain 5 mg, 25 mg and 50 mg of active substance.

The invention claimed is:

1. A process for preparing the compound of formula (I) comprising

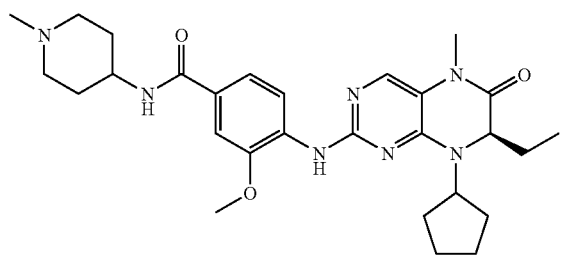
(I)

reacting a compound of formula 4 with a compound of formula 9,

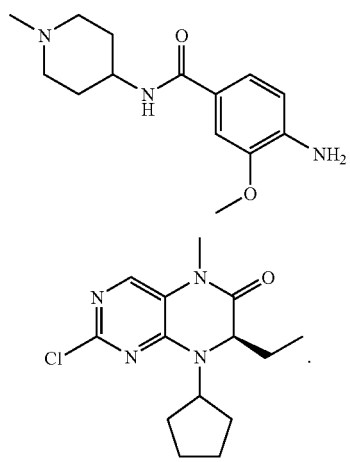
4

9

2. A process for preparing the type I anhydrate of the compound of formula (I)

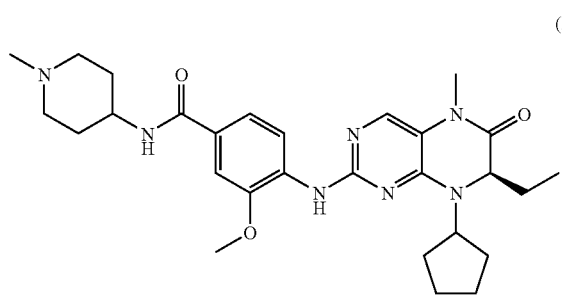
(I)

comprising:
a) preparing a solution of the compound of formula (I) in ethyl acetate and methyl-tert.-butylether,
b) crystallising the type I anhydrate of the compound of formula (I) from the solvent mixture,
c) isolating the type I anhydrate of the compound of formula (I).

3. A process for preparing the type II anhydrate of the compound of formula (I)

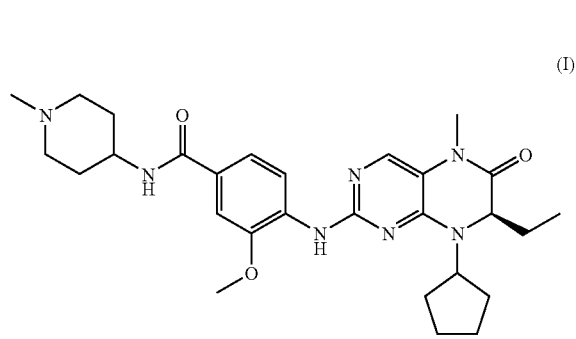
(I)

comprising:
a) preparing a solution of the compound formula (I) in ethyl acetate,
b) crystallising the type II anhydrate of the compound of formula (I) from ethyl acetate followed by the addition of diethyl ether, and
c) isolating the type II anhydrate of the compound of formula (I).

4. A process for preparing the type III anhydrate of the compound of formula (I)

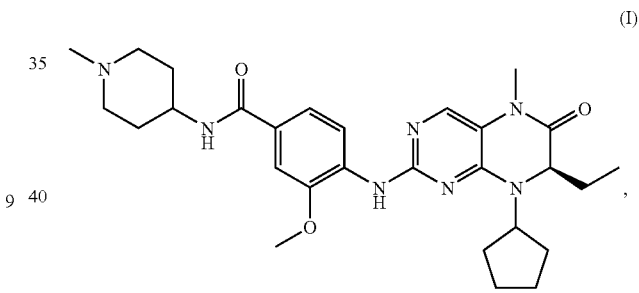
(I)

comprising
(a) rinsing a monohydrate of the compound of formula (I) with dry nitrogen, or
(b) subjecting the monohydrate of the compound of formula (I) to a temperature of about 70° C.

5. The process according to claim 4 wherein for (b) the temperature is about 70 to 120° C.

6. The process according to claim 4 wherein for (b) the temperature is about 70 to 90° C.

7. A compound of formula (I):

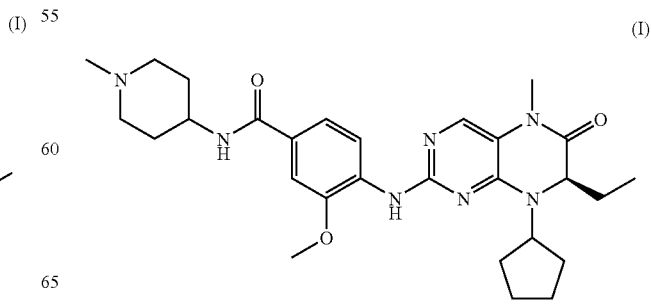
(I)

wherein the compound is a anhydrate.

8. The compound according to claim 7, wherein the compound is an anhydrate type I.

9. The compound according to claim 7, wherein the compound is an anhydrate type II.

10. The compound according to claim 7, wherein the compound is an anhydrate type III.

11. A pharmaceutical composition comprising a therapeutically effective amount of an anhydrate of the formula (I) according to claim 7 and one or more pharmaceutically acceptable excipients.

12. A pharmaceutical composition comprising a therapeutically effective amount of an anhydrate of the formula (I) according to claim 8 and one or more pharmaceutically acceptable excipients.

13. A pharmaceutical composition comprising a therapeutically effective amount of an anhydrate of the formula (I) according to claim 9 and one or more pharmaceutically acceptable excipients.

14. A pharmaceutical composition comprising a therapeutically effective amount of an anhydrate of the formula (I) according to claim 10 and one or more pharmaceutically acceptable excipients.

* * * * *